United States Patent [19]

Sekine et al.

[11] Patent Number: 4,713,487

[45] Date of Patent: Dec. 15, 1987

[54] ETHER CARBOXYLATES AND PROCESS FOR PREPARING SAME

[75] Inventors: Fumimaro Sekine, Wakayama; Tomihiro Kurosaki, Osaka; Toshinao Ukena; Hiroshi Kamitani, both of Wakayama, all of Japan

[73] Assignee: Kao Corporation, Tokyo, Japan

[21] Appl. No.: 865,859

[22] Filed: May 22, 1986

[30] Foreign Application Priority Data

Jun. 6, 1985 [JP] Japan ............................ 60-123315
Jun. 25, 1985 [JP] Japan ............................ 60-138484

[51] Int. Cl.$^4$ .................................... C07C 59/255
[52] U.S. Cl. ................................ 562/587; 562/583
[58] Field of Search ............................ 562/583, 587

[56] References Cited

FOREIGN PATENT DOCUMENTS 2332539 1/1975 Fed. Rep. of Germany ...... 562/583
2808638 8/1978 Fed. Rep. of Germany ...... 562/587
162797 10/1982 Japan ................................ 582/587

OTHER PUBLICATIONS

J. Org. Chem., 47(7) 1298–1302.
Tetrahedron Lett., (52), 5055–5058.

*Primary Examiner*—Paul J. Killos
*Attorney, Agent, or Firm*—Oblon, Fisher, Spivak, McClelland, & Maier

[57] ABSTRACT

Novel ether carboxylates of the following formula (I)

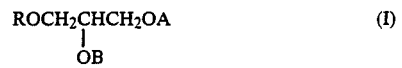

in which R represents a linear or branched alkyl or alkenyl group having from 4 to 32 carbon atoms, and A and B independently represent hydrogen or a —CH$_2$COOM group wherein M represents hydrogen, alkali metal, ammonium, alkanolammonium or lower alkylammonium, provided that A and B are not hydrogen at the same time are prepared by a simple reaction in which a monohaloacetic acid or a salt thereof is reacted with a mono and/or dialcoholate of an alkyl glyceryl ether of the general formula (II)

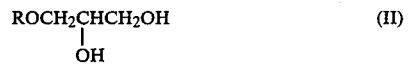

in which R has the same meaning as defined above. Optionally, the resulting product may be converted into a free acid or a salt thereof.

Highly pure ether carboxylates can be produced from inexpensive and readily available starting materials with high yield. The carboxylates are useful as a surfactant of low stimulus and have wide utility in the fields of cosmetics, detergents, medicines, paints and so on.

2 Claims, No Drawings

ETHER CARBOXYLATES AND PROCESS FOR PREPARING SAME

BACKGROUND OF THE INVENTION (1) Field of the Invention

This invention relates to novel ether carboxylates and more particularly, to ether carboxylates useful as surface active agents of low stimulus and a process for preparing the same.

(2) Description of the Prior Art

Surface active agents are compounds which have hydrophobic and hydrophilic groups in the molecule thereof and have wide utility in the fields of cosmetics, starting materials for detergents, medicines, paints, fiber treatments, emulsifiers and the like because of their good fundamental properties such as of moistening, cleaning, emulsification, dispersion and foaming. However, surface active agents are required to have various properties depending on the purpose of use. In particular, when used as household detergents, surface active agents which are mild to the skin, are biologically decomposable, and are free of public nuisance are demanded, but satisfactory surface active agents have not been provided yet.

Under these circumstances in the art, the present inventors made intensive studies and, as a result, found that compounds of the following general formula (I) have a good surface active property and are mild to the skin with good biological decomposability. In addition, the compounds can be prepared by a simple manner using inexpensive and readily available starting materials in high purity and high yield. The present invention was accomplished based on the above findings.

SUMMARY OF THE INVENTION

More particularly, the present invention provides an ether carboxylate of the following formula (I)

$$ROCH_2CHCH_2OA \atop | \atop OB \qquad (I)$$

in which R represents a linear or branched alkyl or alkenyl group having from 4 to 32 carbon atoms, and A and B independently represent hydrogen or a -CH$_2$COOM group wherein M represents hydrogen, alkali metal, ammonium, alkanolammonium or lower alkylammonium, provided that A and B are not hydrogen at the same time. The invention also provides a process for preparing the above compounds.

DETAILED DESCRIPTION OF THE INVENTION AND PREFERRED EMBODIMENTS

In the formula (I), the linear or branched alkyl or alkenyl group represented by R and having from 4 to 32 carbon atoms includes, for example, butyl, octyl, decyl, dodecyl, tetradecyl, hexadecyl, octadecyl, octadecenyl, docosyl, 2-ethylhexyl, 2-hexyldecyl, 2-octylundecyl, 2-decyltetradecyl, 2-undecylhexadecyl, iso-octadecyl and the like. In view of the surface active performance, the group having from 8 to 32 carbon atoms is preferred.

The ether carboxylates (I) of the present invention may be classified into an ether monocarboxylate of the following formula (Ia) or (Ib)

$$ROCH_2CHCH_2OH \atop | \atop OCH_2COOM \qquad (Ia)$$

$$ROCH_2CHCH_2OCH_2COOM \atop | \atop OH \qquad (Ib)$$

in which R and M have the same meanings as defined before, respectively, and an ether dicarboxylate of the following formula (Ic)

$$ROCH_2CHCH_2OCH_2COOM \atop | \atop OCH_2COOM \qquad (Ic)$$

in which R and M have, respectively, the same meanings as defined above.

The ether carboxylates (I) are prepared, for example, according to the following reaction sequence which comprises converting an alkyl glyceryl ether (II) into a mono or dialcoholate (III), reacting a monohaloacetic acid (IV) or a salt thereof with the mono or dialcoholate (III), and converting the resulting product into a free acid or its salt, if necessary.

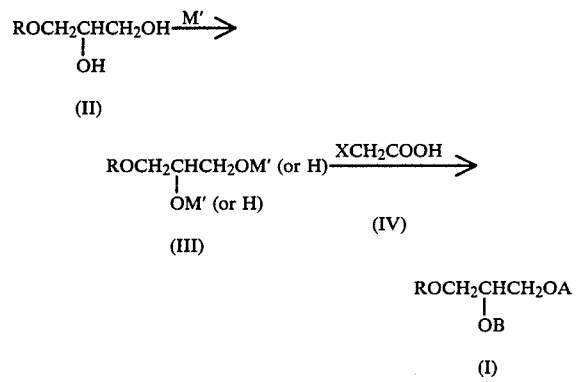

in which M' represents an alkali metal, X represents a halogen atom, and R, A and B have, respectively, the same meanings as defined before.

In order to carry out the process of the invention, an alkyl glyceryl ether (II) is reacted with metallic sodium or sodium hydroxide in a solvent of toluene, xylene, dioxane or a mixture thereof at temperatures not lower than 50° C., preferably from 80° C. to a boiling point of the solvent used, thereby obtaining a corresponding mono or dialcoholate (III). Subsequently, a monohaloacetic acid (IV) or a salt thereof is added to the reaction mixture for carboxymethylation at temperatures not lower than 50° C., preferably from 80° C. to the boiling point of the solvent. The amount of metallic sodium or sodium hydroxide is not critical with respect to the amount of the alkyl glyceryl ether. However, if it is desired to increase the yield of ether monocarboxylates (Ia) and (Ib), the amount of metallic sodium or sodium hydroxide is preferred to be in the range of from 0.7 to 1.3 moles per mole of the alkyl glyceryl ether in order that the monoalcoholates of the following general formulas (IIIa) and (IIIb)

$$ROCH_2CHCH_2OH \atop | \atop OM' \qquad (IIIa)$$

-continued

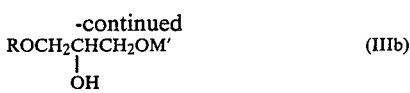

in which each R and each M' have, respectively, the same meanings as defined before, are produced in larger amounts. On the contrary, when the yield of ether dicarboxylate (Ic) is increased, the amount of metallic sodium or sodium hydroxide should preferably be in the range of from 1.0 to 2.0 moles so as to increase an amount of formation of a dialcoholate of the following formula

in which R and M' have, respectively, the same meanings as defined before. The monohaloacetic acid or salts thereof may be added in one or higher equivalents of an alkali. The monohaloacetic acid or salts thereof may be added at an arbitrary rate of addition and may be added to the reaction system at one time or may be added after separation into desired portions.

The resulting reaction product is a mixture of ether monocarboxylates (Ia) and (Ib) and ether dicarboxylate (Ic). If necessary, the product is subjected to column chromatography or separative liquid chromatopography to collect the respective compounds separately.

More particularly, when the reaction product is subjected to separative liquid chromoatography and eluted with a suitable solvent such as, for example, water-methanol, ether dicarboxylate (Ic) is first eluted, followed by ether monocarboxylates (Ia) and (Ib) and finally by the alkyl glyceryl ether, thereby obtaining intended ether carboxylates (I).

For the conversion of the ether carboxylates (I) into other salts, the thus obtained salt is acidified with a mineral acid, such as sulfuric acid, hydrochloric acid or the like, subjected to extraction with a solvent, such as petroleum ether, diethyl ether, hexane or the like, and neutralized with a desired base.

The ether carboxylates (I) of the present invention are novel anionic surface active agents which have an ether bond in the molecule thereof and a good resistance to hydrolysis. Moreover, the carboxylates are mild to the skin and are readily decomposed biologically with a good foaming property and a high solubility in water. In view of these good characteristic properties, the carboxylates can be widely used in various fields.

The present invention is described by way of examples.

EXAMPLE 1

Into a one liter four-necked flask were charged 50.0 g of lauryl glyceryl ether, 300 g of dioxane and 4.5 g of metallic Na, followed by raising the temperature in a stream of nitrogen and agitation at 100° C. for 5 hours to obtain an alcoholate. After cooling down to 50° C., 25.0 g of sodium monochloroacetate was added to the reaction solution, followed by reaction at 100° C. for 3 hours. The solvent was distilled off, after which the reaction solution was subjected to mass separative liquid chromatography to isolate the resulting product while removing unreacted materials (liquid-chromatographic conditions; $SiO_2$ gel column, developing solution water/methanol=1:1). RI was used as a detector, by which disodium lauryl glyceryl ether dicarboxylate was obtained from a first peak, sodium lauryl glyceryl ether monocarboxylate was obtained from a next peak, and lauryl glyceryl ether was obtained from the last peak. Moreover, the solvent was distilled off to obtain the intended sodium lauryl glyceryl ether carboxylates of the following characteristic properties.

(1) Sodium lauryl glyceryl ether monocarboxylate (in the formulas (Ia) and (Ib), $R=-C_{12}H_{25}$ and $M=Na$)

Yield: 14.2 g

| (%) | Elementary analysis: | | | |
| --- | --- | --- | --- | --- |
| | C | H | O | Na |
| found | 60.2 | 9.6 | 23.7 | 6.5 |
| calculated | 60.0 | 9.7 | 23.5 | 6.8 |

NMR ($D_2O$): δ0.93 (d, 3H), 1.28 (bs, 20H), 3.26–3.65 (m, 7H), 3.80–4.06 (m, 2H)

IR (KBr): $cm^{-1}$ 2920, 2850, 1600, 1470, 1430, 1320, 1110 CMC (mol/l): $4.4 \times 10^{-4}$ ($7.0 \times 10^{-3}$)

Krafft point: below 0° C. (15.5)

Foaming strength (ml)*1: 190 (177)

1: The foaming strength was determined under conditions of 40° C. and 4DH using a 1% aqueous solution by a reversing agitation method.

Note: The figures in the parentheses with respect to CMC, Krafft point and foaming strength are reference values for sodium dodecylsulfate.

(2) Disodium lauryl glyceryl ether dicarboxylate (in the formula (Ic), $R=-C_{12}H_{25}$ and $M=Na$)

Yield: 18.7 g

| (%) | Elementary analysis: | | | |
| --- | --- | --- | --- | --- |
| | C | H | O | Na |
| found | 54.2 | 8.0 | 26.8 | 11.3 |
| calculated | 54.3 | 8.1 | 26.7 | 11.0 |

NMR ($D_2O$): δ 0.93 (d, 3H), 1.30 (bs, 20H), 3.20, 3.80 (m, 7H), 3.87 (s, 2H), 4.00 (s, 2H)

IR (KBr): $cm^{-1}$ 2900, 2850, 1600, 1430, 1330, 1120

CMC (mol/l): $2.8 \times 10^{-3}$ ($7.0 \times 10^{-3}$)

Krafft point: below 0° C. (15.5)

Foaming strength (ml): 160 (177)

The monosodium lauryl glyceryl ether moncarboxylate and the disodium lauryl glyceryl ether dicarboxylate obtained in the present invention have the foaming strength comparable to SDS provided as a reference and lower CMC and Krafft point than SDS, thus being considered to be good surface active agents.

EXAMPLE 2

Five grams of the monosodium lauryl glyceryl ether monocarboxylate obtained in Example 1 was dissolved in 50 g of water and acidified with hydrochloric acid, followed by extraction with ether to obtain 4.4 g of lauryl glyceryl ether monocarboxylic acid.

| (%) | Elementary analysis: | | |
| --- | --- | --- | --- |
| | C | H | O |
| found | 64.2 | 10.5 | 25.4 |
| calculated | 64.2 | 10.7 | 25.2 |

Acid value (mg of KOH/g): 176.6 (calculated 176.4)

Hydroxyl value (mg of KOH/g): 175.8 (calculated 176.4)

EXAMPLE 3

Five grams of disodium lauryl glyceryl ether dicarboxylate obtained in Example 1 was dissolved in 50 g of water and acidified with hydrochloric acid, followed by extraction with ether to obtain 4.2 g of lauryl glyceryl ether dicarboxylic acid.

| (%) | Elementary analysis: | | |
|---|---|---|---|
| | C | H | O |
| found | 60.5 | 9.8 | 29.7 |
| calculated | 60.6 | 9.6 | 29.8 |

Acid value (mg of KOH/g): 298.0 (calculated 298.4)

EXAMPLE 4

Into a one liter four-necked flask were charged 50.3 g of octyl glyceryl ether, 300 g of dioxane and 7.1 g of metallic Na, followed by raising the temperature in a stream of nitrogen and agitation at 100° C. for 5 hours to obtain an alcoholate. After cooling down to 50° C., 40.0 g of sodium monochloroacetate was added to the reaction solution, followed by reaction at 100° C. for 5 hours.. The solvent was distilled off, after which the reaction solution was subjected to mass separative liquid chromatography to isolate the resulting product while removing unreacted materials (liquid-chromatographic conditions: $SiO_2$ gel column, developing solution water/methanol=1:1). RI was used as a detector, followed by repeating the procedure of Example 1, thereby obtaining intended sodium octyl glyceryl ether carboxylates of the following characteristic properties.

(1) Monosodium octyl glyceryl ether monocarboxylate (in the formulas (Ia) and (Ib), R=-$C_8H_{17}$ and M=Na)

Yield: 15.3 g

| (%) | Elementary analysis: | | | |
|---|---|---|---|---|
| | C | H | O | Na |
| found | 54.7 | 8.7 | 28.4 | 8.2 |
| calculated | 54.9 | 8.8 | 28.2 | 8.1 |

NMR ($D_2O$): δ0.93 (d, 3H), 1.29 (bs, 12H), 3.30–3.70 (m, 7H), 3.81–4.06 (m, 2H)

IR (KBr): $cm^{-1}$ 2920, 2850, 1610, 1470, 1430, 1310, 1100

(2) Disodium octyl glyceryl ether dicarboxylate (in formula (Ic), R=-$C_8H_{17}$ and M=Na)

Yield: 18.6 g

| (%) | Elementary analysis: | | | |
|---|---|---|---|---|
| | C | H | O | Na |
| found | 49.6 | 7.0 | 30.8 | 12.4 |
| calculated | 49.5 | 7.1 | 30.8 | 12.6 |

NMR ($D_2O$): δ0.93 (d, 3H), 1.28 (bs, 12H), 3.20–3.82 (m, 7H), 3.86 (s, 2H), 3.98 (s, 2H)

IR (KBr): $cm^{-1}$ 2900, 2850, 1600, 1420, 1340, 1120

EXAMPLE 5

Into a one liter four-necked flask were charged 50.1 g of 2-decyltetradecyl glyceryl ether, 500 g of dioxane and 3.0 g of metallic Na, followed by raising the temperature in a stream of nitrogen and agitation at 100° C. for 5 hours to obtain an alcoholate. After cooling down to 50° C., 17.9 g of sodium monochloroacetate was added to the reaction solution, followed by reactin at 100° C. for 5 hours. The solvent was distilled off, followed by dissolution in 200 ml of water and subjecting to mass separative liquid chromatography to isolate the resulting product while removing unreacted materials (liquid-chromatographic conditions: $SiO_2$ gel column, developing solution water/methanol=1:1). RI was used as a detector, followed by repeating the procedure of Example 1, thereby obtaining intended sodium 2-decyltetradecyl glyceryl ether carboxylates of the following characteristic properties. (1) Monosodium 2-decylteradecyl glyceryl ether monocarboxylate (in the formulas (Ia) and (Ib), R=-$CH_2CH(C_{10}H_{23})(C_{12}H_{25})$ and M=Na)

Yield: 11.4 g

| (%) | Elementary analysis: | | | |
|---|---|---|---|---|
| | C | H | O | Na |
| found | 68.5 | 11.1 | 15.8 | 4.7 |
| calculated | 68.5 | 11.2 | 15.7 | 4.5 |

NMR ($D_2O$): δ0.94 (d, 3H), 0.97 (bs, 3H), 1.26 (bs, 41H), 3.28–3.60 (m, 7H), 3.80–4.02 (m, 2H)

IR (KBr): $cm^{-1}$ 2900, 2850, 1600, 1480, 1420, 1300, 1100

(2) Disodium 2-decyltetradecyl glyceryl ether dicarboxylate (in formula (Ic), R=-$CH_2CH(C_{10}H_{23})(C_{12}H_{25})$ and M=Na)

Yield: 15.0 g

| (%) | Elementary analysis: | | | |
|---|---|---|---|---|
| | C | H | O | Na |
| found | 63.2 | 9.9 | 18.8 | 7.9 |
| calculated | 63.3 | 9.9 | 19.0 | 7.8 |

NMR ($D_2O$): δ0.94 (d, 3H), 0.97 (d, 3H), 1.27 (bs, 41H), 3.18–3.79 (m, 7H), 3.86 (s, 2H), 4.00 (s, 2H)

IR (KBr): $cm^{-1}$ 2900, 2860, 1610, 1430, 1330, 1140

What is claimed is:

1. An ether carboxylate of the general formula (Ia) or (Ib)

(Ia)

(Ib)

in which R represents a linear or branched alkyl or alkenyl group having from 4 to 32 carbon atoms and M represents hydrogen, alkali metal, alkanolammonium or lower alkylammonium.

2. An ether carboxylate according to claim 1, wherein R is selected from the group consisting of butyl, octyl, decyl, dodecyl, tetradecyl, hexadecyl, octadecyl, octadecenyl, docosyl, 2-ethylhexyl, 2-hexyldecyl, 2-octylundecyl, 2-decyltetradecyl, 2-undecylhexadecyl, and iso-octadecyl.

* * * * *